(12) United States Patent
Jyothi Prasad et al.

(10) Patent No.: US 8,143,250 B2
(45) Date of Patent: *Mar. 27, 2012

(54) 6-7,DIALKOXY QUINAZOLINE DERIVATIVES USEFUL FOR TREATMENT OF CANCER RELATED DISORDERS

(75) Inventors: Ramanadham Jyothi Prasad, Hyderabad (IN); Bhujanga Rao Adibhatla Kali Satya, Hyderabad (IN); Bollepalli Nageshwara Rao, Hyderabad (IN); Nannapaneni Venkaiah Chowdary, Hyderabad (IN)

(73) Assignee: Natco Pharma Limited, Hyderabad (IN)

( * ) Notice: Subject to any disclaimer, the term of this patent is extended or adjusted under 35 U.S.C. 154(b) by 0 days.

This patent is subject to a terminal disclaimer.

(21) Appl. No.: 12/812,726

(22) PCT Filed: Jan. 18, 2008

(86) PCT No.: PCT/IN2008/000036
§ 371 (c)(1),
(2), (4) Date: Sep. 29, 2010

(87) PCT Pub. No.: WO2009/090661
PCT Pub. Date: Jul. 23, 2009

(65) Prior Publication Data
US 2011/0039844 A1 Feb. 17, 2011

(51) Int. Cl.
*A61K 31/5377* (2006.01)
*C07D 413/12* (2006.01)
*A61P 35/00* (2006.01)

(52) U.S. Cl. ..................... 514/234.5; 544/119
(58) Field of Classification Search ........................ None
See application file for complete search history.

(56) References Cited

U.S. PATENT DOCUMENTS

| 5,183,884 | A | 2/1993 | Kraus et al. |
| 5,332,671 | A | 7/1994 | Ferrara et al. |
| 5,457,105 | A | 10/1995 | Barker |
| 5,475,001 | A | 12/1995 | Barker |
| 5,616,582 | A | 4/1997 | Barker |
| 5,747,498 | A | 5/1998 | Schunur et al. |
| 5,770,599 | A | 6/1998 | Gibson |
| 5,811,098 | A | 9/1998 | Plowman et al. |
| 6,900,221 | B1 | 5/2005 | Norris et al. |
| 2007/0020261 | A1 | 1/2007 | Sliwowski et al. |

FOREIGN PATENT DOCUMENTS

| EP | 0 520 722 A1 | 12/1992 |
| EP | 0 566 226 A1 | 1/1993 |
| EP | 0 602 851 A1 | 12/1993 |
| EP | 6 602 851 A1 | 12/1993 |
| EP | 0 635 498 A1 | 7/1994 |
| EP | 0 635 507 A1 | 7/1994 |
| WO | WO 2005/070909 A1 | 8/2005 |
| WO | WO 2006/090413 A1 | 8/2006 |
| WO | WO 2007/060691 | 5/2007 |
| WO | WO 2007/060691 A2 | 5/2007 |

OTHER PUBLICATIONS

Chapman, caplus an 2010:1161398.*
Arteaga et al., Clinical Cancer Research, vol. 9, 2003, 1579-1589.*
Tarceava, 2011, http://www.gene.com/gene/products/information/oncology/tarceva/.*
Fischer et al., Cancer Treatment Reviews 2007, 33, 391-406.*
Arbiser, The Journal of Clinical Investigation, 117, 10, 2762-2765.*
Madhusudan et al., Clinical Biochemistry, 2004, 37, 618-635.*
Parkinson et al., 2007, caplus an 2007:271009.*
Parkinson et al. "An inhibitor of the epidermal growth factor receptor function does not affect the ability of human papillomavirus 11 to form warts in the xenografted immunodeficient mouse model." *Antiviral Research*. vol. 74. 2007. pp. 4350.
Bradshaw, T.K., "Cell transformation: The role of oncogenes and growth factors," *Mutagenesis* (1986) 1 (2): 91-97.
Larsen, E.R., "New approaches to antitumor therapy," *Annual Reports in Medicinal Chemistry* (1989) 24 (13):121-128.
Cohen et al., "Epidermal growth factor receptor as a therapeutic target in colorectal cancer," *Clinical Colorectal Cancer* (2003) 2 (4): 246-251.
Arteaga, C. L., "ErbB-targeted therapeutic approaches in human cancer," *Experimental Cell Research* (2003) 284: 122-130.
Hunter, T., "A thousand and one protein kinases," *Cell* (1987) 50: 823-829.
Gullick, W.J., "Prevalence of aberrant expression of the epidermal growth factor receptor in human cancers," *British Medical Bulletin* (1991) 47 (1): 87-98.
Sainsbury et al., "Epidermal growth factor receptor status of histological sub-types of breast cancer," *Br. J. Cancer* (1988) 58: 458-460.
Baselga et al., "HER-targeted tyrosine-kinase inhibitors," *Oncology* (2002) 63: 6-16.
Bolen et al., "Analysis of pp60c-src in human colon carcinoma and normal human colon mucosal cells," *Oncogene Research* (1987) 1: 149-168.

* cited by examiner

*Primary Examiner* — Sun Jae Loewe
(74) *Attorney, Agent, or Firm* — Merchant & Gould P.C.

(57) ABSTRACT

In view of the great potential the quinazoline class of compounds offer, we started the synthesis and screening of a large number of new chemical entities with novel structural features. It has been surprisingly and unexpectedly found that quinazolines having 3-Ethynyl anilino group at the 4th position and specifically substituted alkoxy groups in the 6 and 7 positions, impart much enhanced and special anti-proliferative properties when compared to other prominent members of the quinazoline class of drugs. Also, surprisingly the compounds of this invention are much less toxic and the safety profile is exceedingly beneficial for therapeutic applications. The novel chemical entities described in this invention are designated by the general structure (I) and have not been synthesized earlier nor investigated for their therapeutic benefits and safety profile. Compound (I) is NRC-2694, when structure (A).

6 Claims, 8 Drawing Sheets

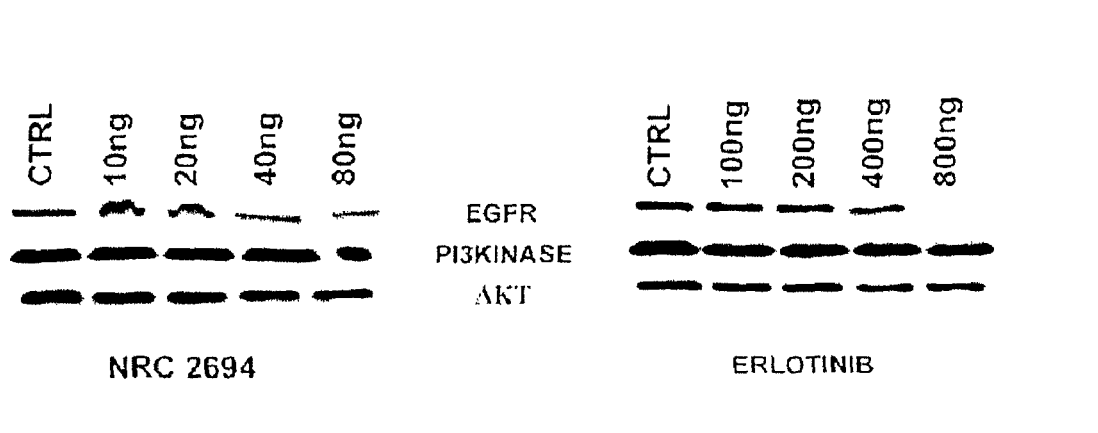
Figure-1: Western blot analysis of A549 cells treated with erlotinib HCl and NRC 2694. Dose dependent decrease in EGFR levels was observed.

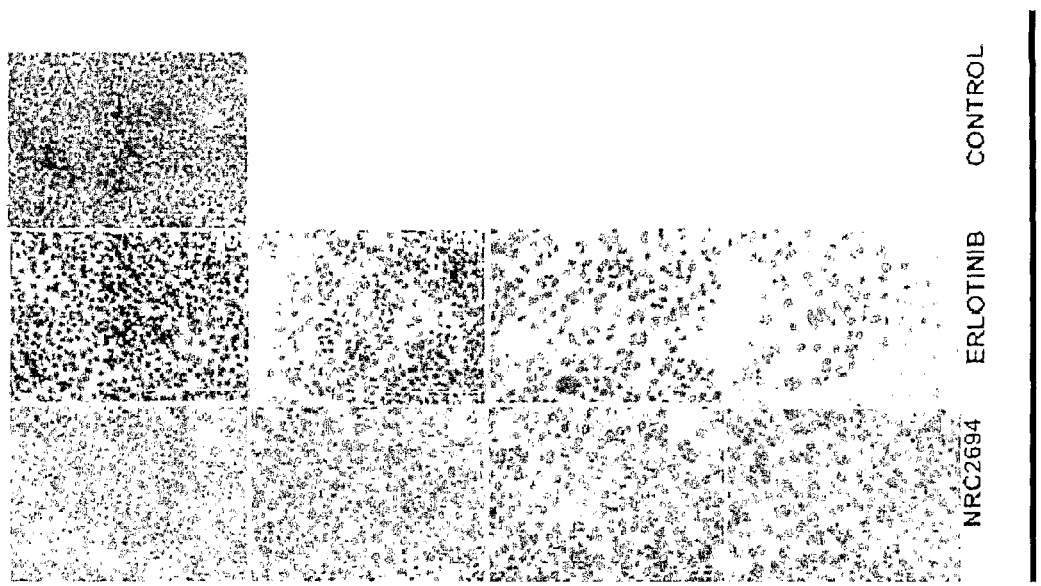
Figure-2: Matrigel invasion assay of H1299 cells treated with Erlotinib and NRC 2694. A dose dependent decrease in invasion was observed

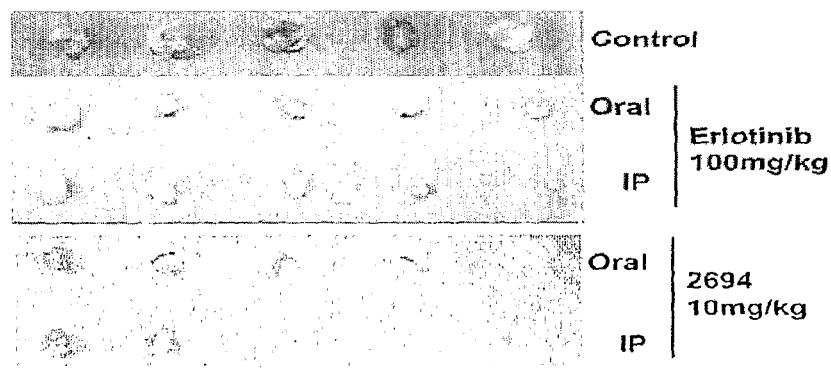
Figure-3: Decrease in tumor size induced by oral and ip administration of Erlotinib HCl and NRC 2694 in nude mice implanted with A549 human lung tumors

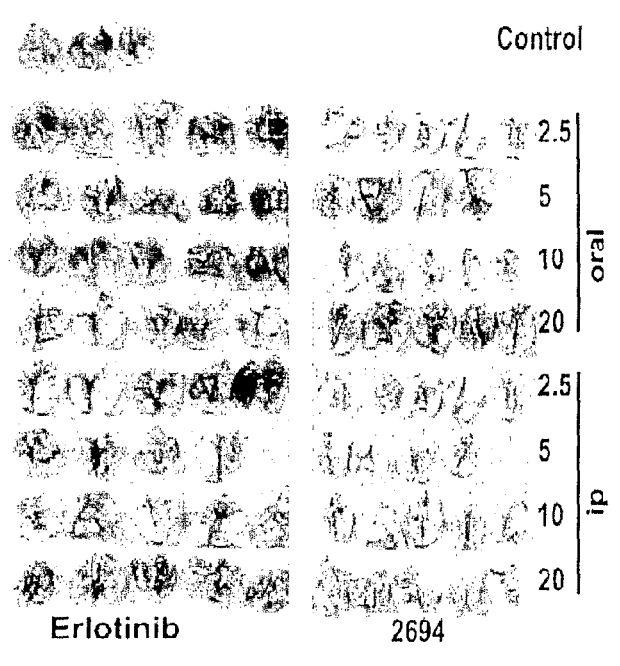
Figure-4: Lungs harvested from nude mice with A549 luciferase expressing cells treated with various concentrations of Erlotinib HCl and NRC 2694 by oral or ip routes

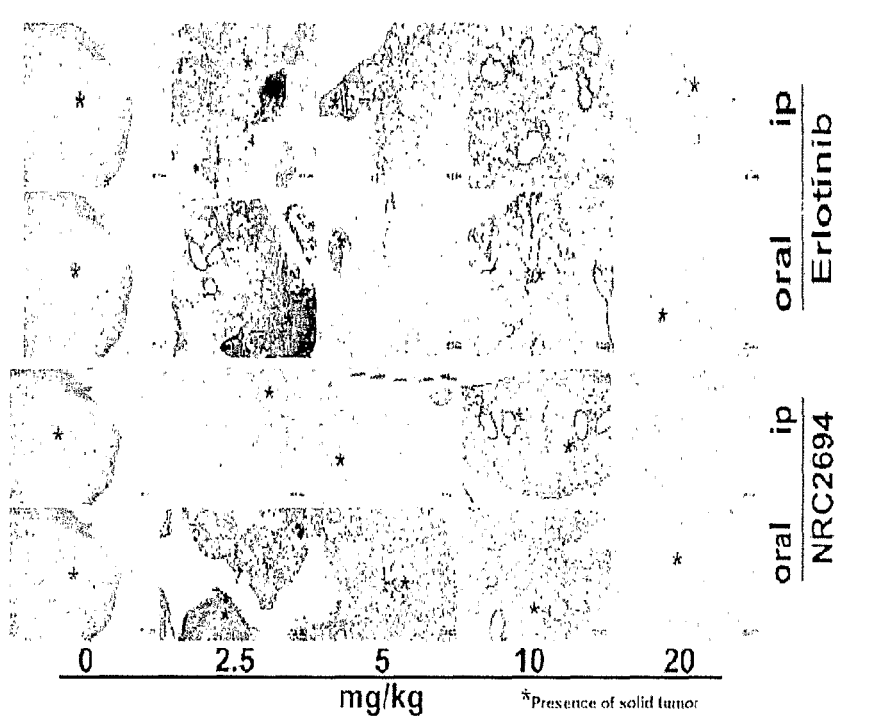
Figure-5: Representative H&E stained sections of nude mice tumor bearing lungs after treatment with Erlotinib HCl and NRC 2694

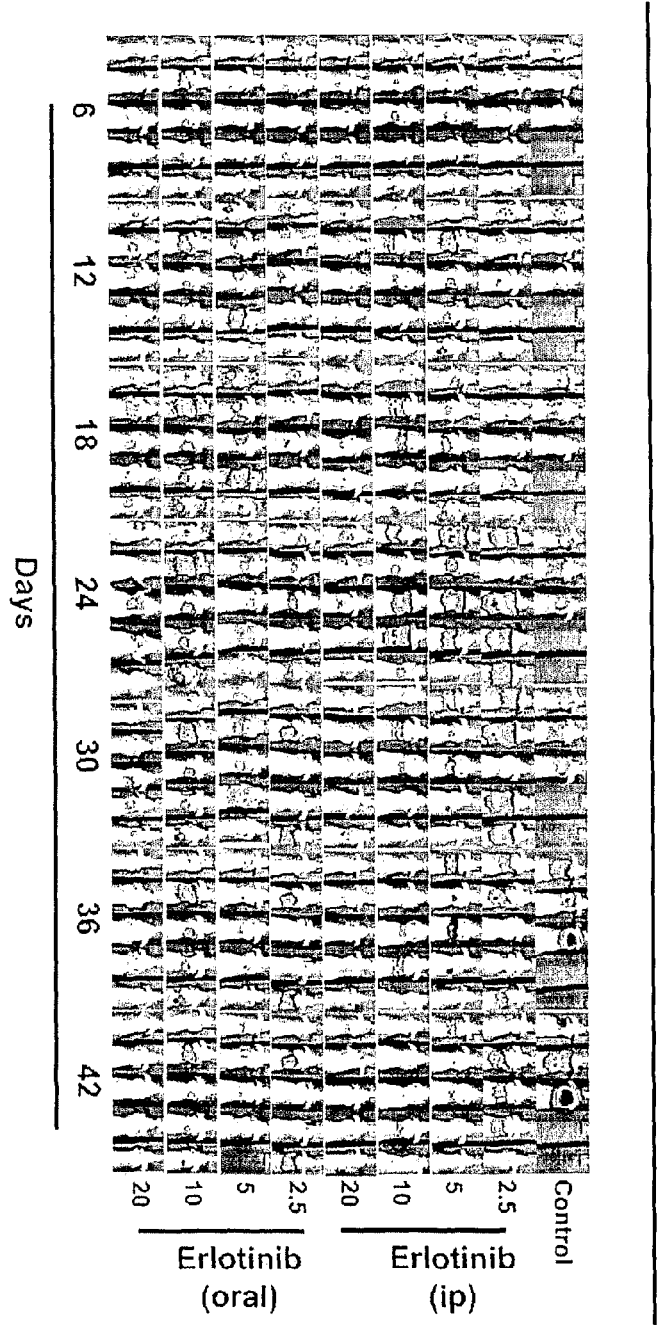
Figure-6: Nude mice implanted with A549 luciferase expressing cells treated with various concentrations of erlotinib HCl by oral and ip routes

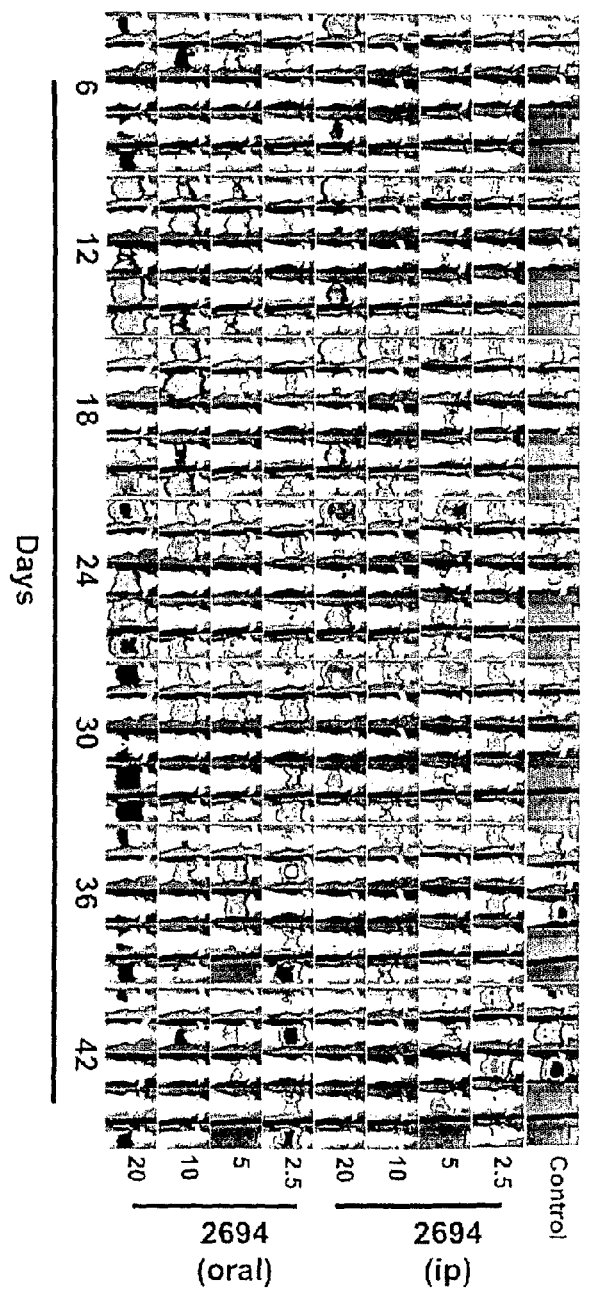
Figure-7: Nude mice implanted with A549 luciferase expressing cells treated with various concentrations of NRC 2694 by oral and ip routes

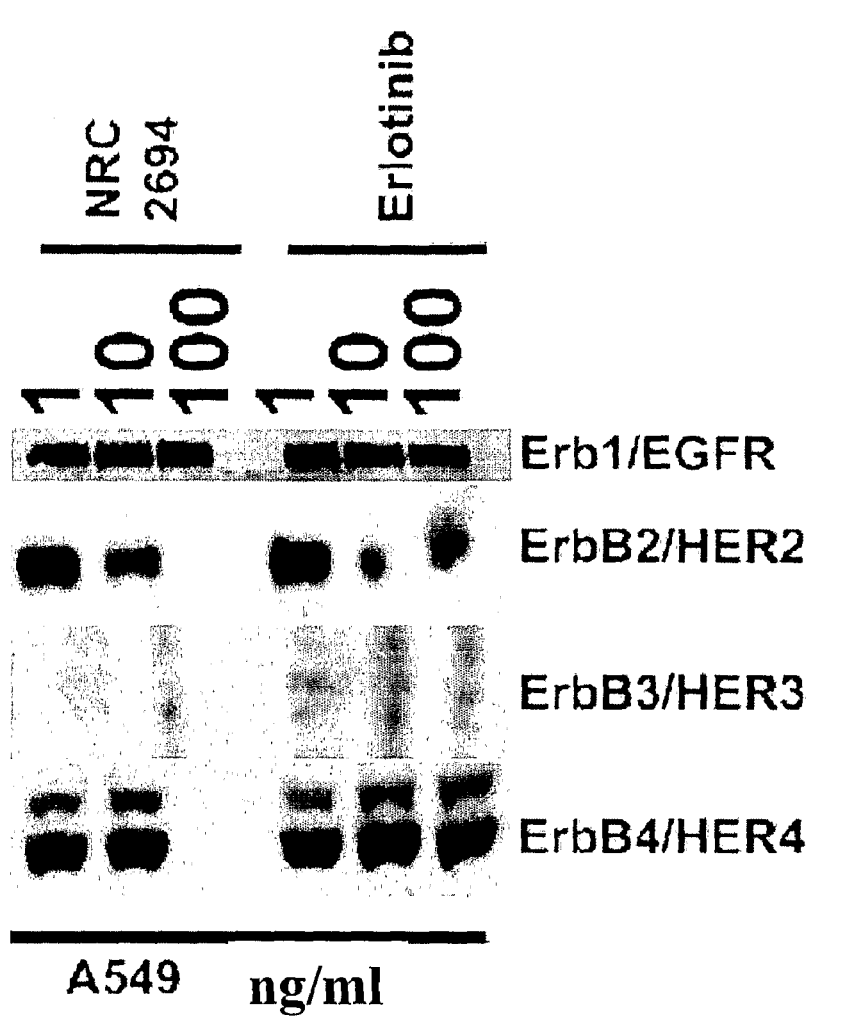
Figure-8: Study of the effect of NRC NCEs in relation to other receptors such as HER-1,2,3,4 and VEGFR *in vitro*
Decrease in levels of Erb1, ErbB2, ErbB3 and ErbB4 after treatment with NRC 2694 in A549 cells was observed

6-7,DIALKOXY QUINAZOLINE DERIVATIVES USEFUL FOR TREATMENT OF CANCER RELATED DISORDERS

This application is a National Stage Application of PCT/IN2008/000036, filed 18 Jan. 2008 and which application is incorporated herein by reference. To the extent appropriate, a claim of priority is made to the above disclosed application.

The invention relates to 6,7-dialkoxy quinazoline derivatives, or pharmaceutically acceptable salts thereof, which possess anti-cancer activity and hence useful in methods of treatment in humans. The invention also relates to processes for the manufacture of the said quinazoline derivatives, and pharmaceutical compositions containing them.

Most of the treatment regimes of the past for cell proliferation diseases such as psoriasis and cancer utilize compounds which inhibit DNA synthesis. Such compounds are toxic to cells and their beneficial effects can be derived only when they show selectivity to rapidly dividing tumour cells.

In recent years it has been discovered that a cell may become cancerous by virtue of the transformation of a portion of its DNA into an oncogene, i.e., a gene which, on activation, leads to the formation of malignant tumour cells (Bradshaw, Mutagenesis, 1986, 1: 91). Several oncogenes encode tyrosine kinase enzymes and that certain growth factor receptors are also tyrosine kinase enzymes (Larsen et al., Ann. Reports in Med. Chem. 1989, Chapt.13).

Receptor tyrosine kinases are important in the transmission of biochemical signals which initiate cell replication. They possess an extra cellular binding domain for growth factors such as an epidermal growth factor and an intracellular portion which functions as a kinase to phosphorylate tyrosine amino acids in proteins and hence to influence cell proliferation. It is also known that such kinases are frequently present in common human cancers such as breast cancer (Sainsbury et al., Brit. J. Cancer, 1988, 58: 458), gastro intestinal cancers such colon, rectal and stomach cancers (Bolen et al., Oncogene Res., 1987, 1: 149). It is discovered that Tyrosine Kinase activity (TK activity) is more frequently detectable in malignant cells than in normal cells (Hunter, Cell, 1987, 50: 823).

More recently, it has been shown that Epidermal Growth Factor Receptor (EGFR) which possesses TK activity is over expressed in many human cancers such as brain, lung squamous cell, bladder, gastric, breast, head & neck, oesophageal, thyroid and the like. (W. J. Gullick, Brit. Med. Bull. 1991; 47: 87). The Epidermal Growth Factor Receptor (EGFR), a member of Receptor Tyrosine Kinase (RTK) family comprises of four receptors Erb1/HER1, Erb/HER2, Erb/HER3 and Erb/HER4.

An important strategy to inhibit EGFR-TK activity has been exploiting small synthetic molecules (Arteaga C L, Exp. Cell Res., 2003, 284: 122-130). Certain quinazoline derivatives like gefitinib (Iressa™, Astra Zeneca); erlotinib (OSI-774, Tarceva™), PD-183805, PKI-166, EKB-569, PD-168393, CGP-59362 have been have been extensively investigated for possible treatment options for several forms of cancer (Baselga et al., Oncology 2002, 63: 6-16, Cohen R B., Clin. Colorectal Cancer, 2003, 2: 246-251). The European patent applications namely EP 0566226, EP0602851A$_1$, EP 0635507 A$_1$, EP 0635498 A$_1$, EO 0520722 A$_1$ disclosed certain quinazoline derivatives possessing anti-cancer properties as a result of their TK inhibitory property.

US patents U.S. Pat. Nos. 5,475,001, 5,457,105, 5,616, 582, 5,770,599, 5,747,498, 6,900,221 etc. deal with quinazoline derivatives with structural features such as a substituted anilino moiety in the 4-position and a variety of functionalized alkyl groups in the 6- and 7-positions of the quinazoline nucleus.

Specifically U.S. Pat. Nos. 5,457,105, 5,616,582 deal with N-(3-Chloro-4-fluorophenyl)-7-methoxy-6-[3-(4-morpholinyl)propoxy]-4-quinazolinamine (Gefitinib) and U.S. Pat. No. 5,747,498 and 690,221 deal with N-(3-Ethylnylphenyl)-6,7-bis(2-methoxyethoxy)-4-quinazolinamine (Erlotinib). WO 20005/070909, WO 2007/060691 A$_2$ and WO 06/090413 deal with variations in synthesis or polymorphic forms of these two popular anti-cancer drugs.

In view of the great potential the said quinazoline class of compounds offer, we started the synthesis and screening of a large number of new chemical entities with novel structural features. It has been surprisingly and unexpectedly found that quinazolines having 3-Ethynyl anilino group at the 4th position and specifically substituted alkoxy groups in the 6 and 7 positions, impart much enhanced and special antiproliferative properties when compared to other prominent members of the quinazoline class of drugs. Also, surprisingly the compounds of this invention are much less toxic and the safety profile is exceedingly beneficial for therapeutic applications. The novel chemical entities described in this invention are designated by the general structure (I) and have not been synthesized earlier nor investigated for their therapeutic benefits and safety profile.

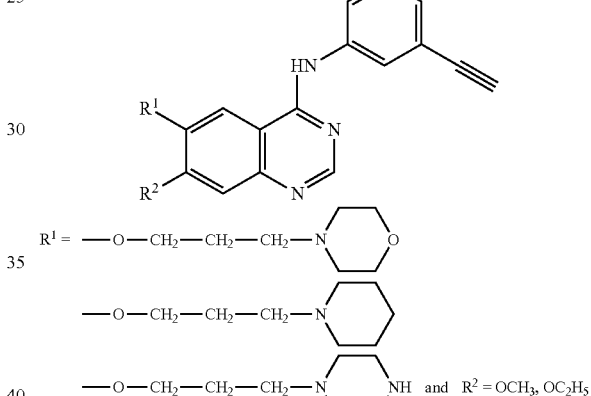

Compound (I) is NRC-2694, when

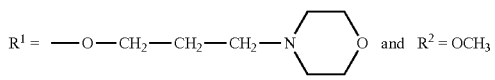

Mono HCl salt of NRC-2694 is NRC-2694 A. DiHCl salt of NRC-2694 is NRC-2694 B. The novel compounds of this invention especially NRC-2694 have unexpected superior anti-cancer/anti-proliferative properties and offer additional therapeutic benefits in comparison to prominent drugs of this class as detailed below:

1) Lower inhibitory concentration: The inhibitory concentration (IC$_{50}$) in MTT proliferation assay method indicated a value in the range 40-90 ng/ml (100-200 nm) whereas erlotinib HCl has a value of 836 ng/ml (1945 nm). The same has been confirmed by western blot analysis and Matrigel invasion assay.
2) Complete tumor regression: Complete tumor regression was observed by oral administration of the compounds in nude mice implanted with A549 human lung tumor cells at 10 mg/Kg dose. In the comparative study, even at 100 mg/Kg dose, erlotinib HCl could not induce complete tumor regression. Visual examination of lung tissue of the mice implanted with A549 and luciferase expression experiments confirmed the same observations.

3) Drug effectiveness: Evaluation of effective dose indicated a value ($ED_{50}$) of 6.3 mg/Kg for a typical compound of this invention viz., NRC-2694 whereas the value obtained with erlotinib HCl was 22 mg/Kg.

A curative effect of 100% has been observed with NRC-2694 as against 50-60% only in the case of erlotinib HCl.

4) Additional unique indications: Compounds of this invention typically NRC-2694, exhibited additional indications like down regulating expression levels of ErbB2, ErbB3, ErbB4 and VEGFR receptors. This special, very prominent and surprising result is totally unexpected and was not seen at all with erlotinib HCl.

5) Safety profile: The safety profile of compounds of this invention, typically NRC-2694 is quite promising and unexpectedly wide and extremely beneficial. Thus, NRC-2694 exhibited a Maximum Tolerated Dose (MTD) of 500 mg/Kg as against 2000 mg/Kg for erlotinib HCl.

The wide therapeutic window offered by NRC-2694 was demonstrated by its $LD_0$ value 25, of 2000 mg/Kg as against 500 mg/Kg for erlotinib HCl. The $LD_{50}$ value could not be pinpointed for NRC-2694, whereas a value of 805 mg/Kg was determined for erlotinib HCl.

The following examples are given for the purpose of illustrating the process for preparing compounds of the present invention and their superior biological efficacy and therefore should not be considered to limit the scope or spirit of the invention. (Scheme-1)

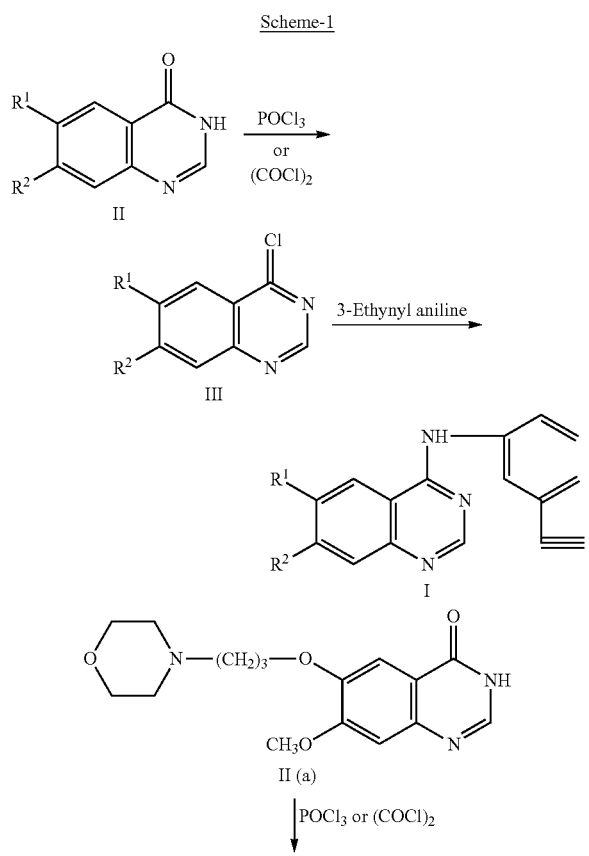

Scheme-1

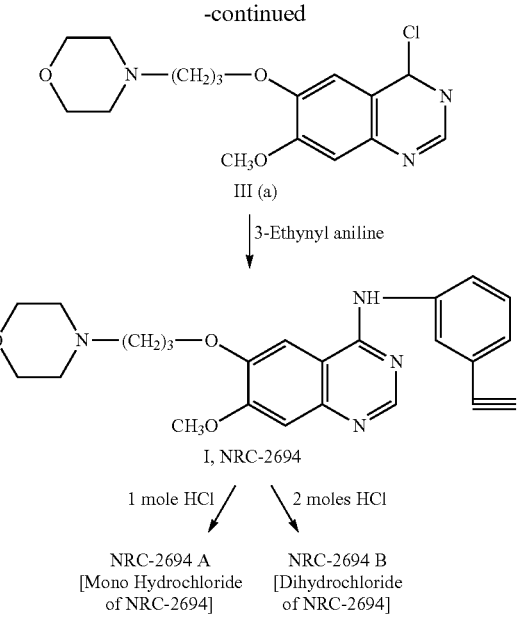

EXAMPLE-1

Preparation of N-(3-ethylnylphenyl)-7-methoxy-6-[3-(4-morpholinyl)propoxy]-4-quinazolinamine (I, NRC-2694)

i) Preparation of 4-Chloro-6-[3-(4-morpholinyl)propoxy-4-quinazoline (IIIa)

Into a clean and dried 5-Liter four necked round bottomed flask equipped with a mechanical stirrer, reflux-condenser, pressure equalizing addition funnel, and thermometer socket were charged chloroform (3000 ml), dimethyl formamide (30 ml) followed by 7-methoxy-6-(3-morpholino propoxy)-3,4-dihydro-quinazolin-4-one (IIa) (150 g), obtained according to the process given in Example-1 of PCT international application published as WO.2005/070909A1. Oxalyl Chloride (120 g) was slowly added and the reaction mass was heated to reflux temperature and maintained at reflux temperature for about 5 hours. Reaction was found to be completed by HPLC test. The solvent chloroform and excess oxalyl chloride were distilled off by applying mild vacuum. The reaction mass was cooled to about 40° C. and added chloroform (300 ml) and again distilled out the solvent by applying mild vacuum. The reaction mixture was cooled to room temperature and acetonitrile (3000 ml) was added and stirred for 10-15 minutes and kept under nitrogen atmosphere to proceed to the next step.

ii) Preparation of N-(3-ethylnylphenyl)-7-methoxy-6-[3-(4-morpholinyl)propoxy]-4-quinazolinamine (I, NRC-2694)

Into a 5-Liter four necked round bottomed flask equipped with a mechanical stirrer, reflux-condenser and thermometer socket containing the chloro compound in acetonitrile from the above step-(i); 3-ethynyl aniline (69 g) was added slowly in about 10-15 minutes and the reaction mass was heated to reflux temperature and maintained at reflux temperature for about 4 hrs. The reaction was found to be completed by HPLC test. Then the reaction mass was cooled to 25-35° C. and filtered, washed the cake with acetonitrile (500 ml) and dried the cake.

The above dried crude compound was taken into a another 5 liter round bottomed flask and charged water (2500 ml) and slowly raised the temperature to 60-65° C. and was adjusted the pH of the reaction mass to 10-12 with dilute sodium hydroxide solution. The solid product separated was filtered and washed with water and dried at 70-75° C. to get 173.0 g of N-(3-ethynylphenyl)-6-(3-morphiline propoxy)-7-methoxy-4-quinazolamine as a off-white solid.

iii) Recrystallisation of Preparation of N-(3-ethylnylphenyl)-7-methoxy-6-[3-(4-morpholinyl)propoxy]-4-quinazolinamine from Toluene Into a 5-Liter four necked round bottomed flask equipped with a mechanical stirrer, reflux-condenser and thermometer socket were charged toluene (3750 ml), followed by N-(3-ethynylphenyl)-6-(3-morpholino propoxy)-7-methoxy-4-quinazolinamine (50 g) obtained by the process described in the above given example-(1). The reaction mixture was heated to 90-95° C., so that the solid completely dissolved. Then carbon treatment was given and filtered. The filtrate was cooled to 25-35° C., maintained for about 1 hour and filtered and dried the material to get 40.15 g of N-(3-ethylnylphenyl)-7-methoxy-6-[3-(4-morpholinyl)propoxy]-4-quinazolinamine as a white crystalline solid.

mp: 185-187° C.
Purity: 99.72% (HPLC)
IR (KBr) (cm$^{-1}$): 3280.9, 2954.6, 2810.3, 1620.1, 1604.2, 1572.1, 1527.7, 1505.2, 1484, 1430.5, 1388.2, 1247.5, 1211.2, 1140.3, 1110.4, 1010.3, 953.4, 859.6, 784.2 Cm$^{-1}$
$^1$HNMR
(300 MH$_z$; DMSO-d$_6$): 9.57 (s, 1H); 8.48 (s, 1H); 7.99 (s, 1H); 7.86 to 7.92 (d, 2H); 7.34 to
7.44 (t, 1H) 7.18 to 7.21 (s, 2H); 4.15 to 4.21 (t, 4H); 3.92 (s, 3H) 3.5
to 3.6 (t, 4H); 2.4 to 2.52 (m, 5H); 1.95 to 2.01 (m, 2H).
Mass: 419.4 (M+1)

EXAMPLE-2

Recrystallisation of N-(3-ethylnylphenyl)-7-methoxy-6-[3-(4-morpholinyl)propoxy]-4-quinazolinamine from Acetonitrile Into a two liter three necked round bottomed flask equipped with a mechanical stirrer, reflux-condenser and thermometer socket were charged acetonitrile (1000 ml), followed by N-(3-ethylnylphenyl)-7-methoxy-6-[3-(4-morpholinyl)propoxy]-4-quinazolinamine (25 g) obtained from the process described in the above given Example-(1). The reaction mass was slowly heated to 65-70° C., so that the solid material completely dissolved and carbon treatment was given and filtered. The filtrate was transferred into another round-bottomed flask and slowly cooled to 10-15° C. and maintained for 30 minutes at that temperature. The mass was filtered and after washing the cake with chilled acetonitrile dried to get 20.50 g of N-(3-ethylnylphenyl)-7-methoxy-6-[3-(4-morpholinyl)propoxy]-4-quinazolinamine as a white crystalline solid.

mp: 186-187° C.
Purity: 99.68% (HPLC)

EXAMPLE-3

Recrystallisation of N-(3-ethylnylphenyl)-7-methoxy-6-[3-(4-morpholinyl)propoxy]-4-quinazolinamine from Ethyl acetate Into a three liter three necked round bottomed flask equipped with a mechanical stirrer, reflux-condenser and thermometer socket were charged ethyl acetate (2000 ml), followed by N-(3-ethylnylphenyl)-7-methoxy-6-[3-(4-morpholinyl)propoxy]-4-quinazolinamine (25 g) obtained from the process described in the above given Example-(1). The reaction mass was slowly heated to 65-70° C., so that the solid material completely dissolved and carbon treatment was given and filtered the reaction mass. The filtrate was transferred into another round-bottomed flask and slowly cooled to 10-15° C. and maintained for 30 minutes at that temperature. The crystalline mass was filtered and after washing the cake with chilled ethyl acetate dried to get 20.95 g of N-(3-ethynlphenyl)-6-(3-morpholino propoxy)-7-methoxy-4-quinazolinamine as a white crystalline solid.

mp: 185-187° C.
Purity: 99.7% (HPLC)

EXAMPLE-4

Preparation of N-(3-ethylnylphenyl)-7-methoxy-6-[3-(4-morpholinyl)propoxy]-4-quinazolinamine mono hydrochloride. (NRC-2694A)

Into a 500 ml three necked round bottomed flask equipped with a mechanical stirrer, reflux-condenser, thermometer socket etc. charged Isopropyl alcohol (250 ml), followed by N-(3-ethylnylphenyl)-7-methoxy-6-[3-(4-morpholinyl)propoxy]-4-quinazolinamine (5 g), obtained from the process given in Example-1. The temperature of the reaction mass was raised to 65-70° C. so that all the solid material dissolves and carbon treatment was given and filtered. The filtrate was cooled to about 55 to 60° C. and to this one mole equivalent of HCl-gas dissolved in isopropyl alcohol solution was added when the mono hydrochloride salt separated out. The reaction mass was maintained at reflux temperature for about 2 hrs and then cooled to room temperature and filtered and dried to get 5.1 g. of N-(3-ethynyl phenyl)-6-(3-morpholino propoxy)-7-methoxy-4-quinazolinamine mono hydrochloride as a white crystalline substance.

Purity: 99.8% (HPLC)
HCl content
(chemical): 8.19% (Theoretical value: 8.01%)
IR (KBr) (cm$^{-1}$) 3407, 3305, 3259.5, 2934, 2619, 1625.9, 1593.8, 1579.9, 1530.8, 1512,
1476.9, 1392.2, 1356.8, 1282.1, 1242.1, 1207.9, 1141.3, 1100.8,
1076.1, 1042.1, 1026.5, 1011.5, 957.7, 941.5, 922.1, 857.3, 852, 838.1, 796, 782.4,

EXAMPLE-5

Preparation of N-(3-ethylnylphenyl)-7-methoxy-6-[3-(4-morpholinyl)propoxy]-4-quinazolinamine di hydrochloride (NRC-2694B)

Into a 500 ml three necked round bottomed flask equipped with a mechanical stirrer, reflux-condenser and thermometer socket were charged Isopropyl alcohol (250 ml), followed by N-(3-ethylnylphenyl)-7-methoxy-6-[3-(4-morpholinyl)propoxy]-4-quinazolinamine (5 g), obtained from the process given in Example-1. The temperature of the reaction mass was raised to 65-70° C. so that all the solid material dissolves. Carbon treatment was given and filtered. The filtrate was cooled to about 55 to 60° C. and to this two moles equivalent of HCl-gas dissolved in isopropyl alcohol solution was added when the dihydrochloride salt separated out. The reaction mass was maintained at reflux temperature for about 2 hrs and then cooled to room temperature and filtered and dried to get 5.5 g. of N-(3-ethylnylphenyl)-7-methoxy-6-[3-(4-morpholinyl)propoxy]-4-quinazolinamine di hydrochloride as a white crystalline substance.

Purity 99.78% (HPLC)

HCl content (chemical): 14.9% (Theoretical value: 14.83%)

IR (KBr) (cm$^{-1}$): 3406.8, 3194.1, 2942.7, 2681.9, 2623.6, 1633.7, 1566.2, 1528.6, 1512.5, 1438.6, 1359.6, 1282.3, 1218.3, 1157.1, 1132.7, 1105.9, 1075.6, 1001.9, 942.1, 875.3, 816.1, 787.2

EXAMPLE-6

Maximum Tolerated Dose (MTD) and Acute Toxicity Evaluation (Tables 1 &2)

The MTD Early citation study was done in male and female Swiss Albino mice (weighing 20-25 gm).

The study was done as per OECD guidelines rule 420, the study was conducted between 9 am to 5 pin to avoid circadian cycle, the compounds Erlotinib and NRC-2694 were suspended with 2% gum acacia, the compounds were administered in doses of 5, 50, 300 and 2000 mg/Kg (po) orally. The intermediate doses were administered depending upon mortality. The animals were observed for gross behavioral changes at every hour up to six hours after drug administration. The animals further observed up to 72 hours for mortality if any. The survived animals were autopsied for asserting the absorption of compound through g.i.t.

Acute toxicity of Erlotinib and NRC-2694 was carried out in male and female mice. The doses 500, 750, 1000 and 2000 mg/Kg were administered orally. Each group consists of 5 mice. The animals were observed for mortality for 14 days after compound administration. The survived animals were autopsied for asserting the absorption of compound through g.i.t.

The $LD_{50}$ was determined using Litchfield and Wilcoxon (J. Pharmacol. Exp. Ther. 1949, 96: 99-113).

The results of the toxicity studies are tabulated in Tables-1&2. The Maximum Tolerated Dose (MTD) of erlotinib HCl was found to be 500 mg/Kg (po) whereas for NRC-2694, it is 2000 mg/Kg (po). Similarly, $LD_0$ was found to be 500 mg/Kg (po) for erlotinib HCl and 2000 mg/Kg (po) for NRC-2694. Thus, the unexpected and surprisingly low toxicity and safety profile of NRC-2694 over erlotinib HCl has been established.

TABLE 1

Comparative (mtd) of erlotinib. HCl and NRC-2694 (mice) early citation study

| Compound | MTD mg/Kg (po) |
|---|---|
| Erlotinib HCl | 500 |
| NRC2694 | 2000 |

TABLE 2

Acute $LD_{50}$ studies (single dose 7 days observation) in mice

| Compound | $LD_0$ mg/Kg (po)* | $LD_{50}$ mg/Kg (po) |
|---|---|---|
| Erlotinib HCl | 500 | 805 |
| NRC2694 | 2000 | — |

*$LD_0$: No mortality was observed at end of 7 days.

EXAMPLE-7

In vitro and in vivo Evaluation Studies and Evaluation of Therapeutic Efficacy

Samples: Erlotinib was used as a control reference drug, biological activity of new compounds of this invention were tested in comparison with this drug as positive control.

i) MTT Proliferation Assay:

MTT [3-(4,5-dimethylthiazol-2-yl)-2,5-diphenyltetrazolium bromide] assay, first described by Mosmann in 1983, is based on the ability of mitochondrial dehydrogenase enzyme from viable cells to cleave the tetrazolium rings of the pale yellow MTT and form dark blue formazan crystals largely impermeable to cell membranes, thus resulting in its accumulation within healthy cells. Solubilization of the cells by the addition of a detergent results in the liberation of the crystals, which are solubilized. The number of surviving cells is directly proportional to the level of the formazan product created. The color can then be quantified using a simple colorimetric assay. This assay was done using 0-1000 ng/ml concentrations of Erlotinib and the test compounds in A549 and H1299 cells. The protocol was based on ATCC and as per manufacturer's instructions (Catalog No.: 30-1010K)

From the MTT proliferation assay, it was determined that the inhibiting concentration ($IC_{50}$) of compounds of invention varied from 40-90 ng/ml (100-200 nm) whereas 'Erlotinib hydrochloride' used as a positive control has a value as high as 836 ng/ml (1945 nm). Thus it is derived that the novel compounds of this invention are at least 10 times more potent than erlotinib hydrochloride.

ii) Western Blot Analysis: (FIG. 1)

Ideal drug concentrations determined from the MTT proliferation assay were used to treat $1 \times 10^6$ H1299 or A549 cells in appropriate media for 72 hr following which cell lysates were extracted and fractionated on a 10% SDS PAGE gel under reducing conditions. The gels were blotted onto treated nylon membranes (Biorad) and immunoprobed for EGFR, P13K and AKT.

Significant change in EGFR expression are observed in a dose dependent manner. NRC-2694 at 80 ng (190 nm) concentrations caused comparable inhibition of EGFR expression with erlotinib HCl at 800 ng (1860 nm) concentrations. The ten fold level of efficacy of NRC-2694 is thus evident.

iii) Matrigel Invasion Assay: (FIG. 2)

The in vitro invasiveness of H1299 and A549 cells in the presence of various concentrations of NRC compounds (as determined by MTT assay) was assessed using a modified Boyden chamber assay. Cells were treated with these compounds for 48 hr. $1 \times 10^6$ cells were suspended in 600 µl of serum-free medium supplemented with 0.2% BSA and placed in the upper compartment of the transwell chambers (Corning Costar Fisher Scientific cat #07-200-158, Pittsburgh Pa.) coated with matrigel (0.7 mg/ml). The lower compartment of the chamber was filled with 200 µl of serum medium and the cells were allowed to migrate for 24 h. after incubation, the cells were fixed and stained with Hema-3 and quantified as previously described (Mohanam et al. 1993). The migrated cells were quantified as percent invasion. The compound NRC-2694 showed significant decrease in invasion in a dose dependent manner.

iv) In vivo Evaluation on Subcutaneous Lung Tumours in Nude Mice (FIG. 3):

Nude mice were implanted with $2 \times 10^6$ A549 cells in the right hind limb flank. Upon the observance of a tumour (>2 mm), mice were given oral or ip treatments of the test compounds including erlotinib HCl used as positive control. A dose of 100 mg/Kg of erlotinib HCl was identified as the base line dose.

Tumour sizes were measured and complete regression of tumours were observed in the mice treated with NRC-2694 at 10 mg/Kg dose. However tumours were still present in the control group treated similarly with erlotinib HCl even at 100 mg/Kg dose level. Thus, a ten fold superiority in efficacy of the compound of this invention (NRC-2694) has been established.

v) Evaluation of Lung Tissue Harvested from Nude Mice after Treatment: (FIG. 4)

Lungs harvested from nude mice implanted with A549 luciferase expressing cells treated with various concentrations of erlotinib HCl and NRC-2694 by oral/ip routes were examined for residual tumours.

Complete regression of tumours was observed in the treatment group with NRC-2694, whereas tumours were still present in the group treated with erlotinib HCl, thus establishing the unexpected surprisingly superior efficacy of the compounds of this invention.

vi) Examination by Visualization of Tumors in Lung Tissue: (FIG. 5)

Nude mice were implanted by intrapulmonary injections of A549 cells. The mice were treated with oral/ip routes by erlotinib HCl and NRC 2694 at 2.5 and 20 mg/Kg doses. Thirty days after daily drug treatments, mice were sacrificed and lungs harvested. The lung tissues were fixed in 10% buffered formaldehyde, paraffin embedded and sectioned. The sections were H&E stained as per statutory protocols to visualize solid or diffuse tumors.

The group treated with NRC 2694 fared much better than those treated with erlotinib HCl at all dose levels thus establishing the superior efficacy of NRC 2694.

vii) Nude Mice Implanted with A549 Luciferase Expressing Cells: (FIGS. 6 &7)

Nude mice implanted with A549 luciferase expressing cells treated with various concentrations of erlotinib HCl and NRC 2694 by oral and ip routes were observed for tumors and the pictorial observations are given as FIG. 6 and FIG. 7. It was observed that the group treated with NRC 2694 fared much better than the group treated with erlotinib HCl. No tumors were observed at the end of 42 days treatment with NRC 2694 whereas residual tumors were still present in the group treated with erlotinib HCl both by oral and ip routes.

viii) Curative Effect from in vivo Studies in Nude Mice:

The curative effect as a ratio of number of animals cured to the number of animals used in the study is tabulated and presented in Table-3.

TABLE 3

Curative effect of NRC-2694 and erlotinib HCl on lung cancer

| Drugs | Concentration Mg/Kg | Cure ratio |
|---|---|---|
| Erlotinib IP | 2.5 | 1/5 |
|  | 5 | 2/5 |
|  | 10 | 2/5 |
|  | 20 | 3/5 |
| Erlotinib oral | 2.5 | 2/5 |
|  | 5 | 0/5 |
|  | 10 | 1/5 |
|  | 20 | 2/5 |
| NRC 2694 IP | 2.5 | 1/5 |
|  | 5 | 1/5 |
|  | 10 | 3/5 |
|  | 20 | 5/5 (100%) |
| NRC 2694 oral | 2.5 | 1/5 |
|  | 5 | 2/5 |
|  | 10 | 3/5 |
|  | 20 | 3/5 |

It can be seen that the ratio is close to 100% in the case of NRC 2694 whereas the ratio is between 40-60% in the case of study group with erlotinib HCl.

ix) Evaluation of $ED_{50}$:

The $ED_{50}$ values were evaluated based on the lung section and tumor regression studies. A value of 6.3 mg/Kg was calculated for NRC 2694 whereas the value obtained for erlotinib HCl was 22 mg/Kg by oral route. Thus the superior efficacy of the compound of the present invention is established.

x) Study with Other Receptors Such as Her-1, Her-2, Her-3, Her-4 and VEGFR in vitro (FIG. 8):

To determine the effect of NRC 2694 on the various other receptors of EGFR family (Erb/HER), human lung cancer cells A549 were treated with various concentrations of NRC 2694 along with erlotinib HCl for a side-by-side comparison. Levels of Erb-1, Erb-2, Erb-3, Erb-4 and VEGFR were determined by western blot analysis.

It was observed that NRC 2694 down regulated levels of Erb B2, Erb B3, Erb B4 and VEGFR levels effectively whereas no such indication was seen with erlotinib HCl. The additional inhibitory indication in the expression levels of the above mentioned receptors is clearly demonstrative of the unexpected and surprising property of the principal molecule of this invention viz., NRC 2694.

xi) Conclusion:

The unexpected, surprising and superior anti-tumor properties and additional therapeutic potential of the compound of the present invention is thus established in the above experiments in comparison to erlotinib HCl.

EXAMPLE-8

The following is an illustrative representative pharmaceutical dosage form containing the compound of formula NRC-2694 or a pharmaceutically acceptable salt thereof, for therapeutic of prophylactic use in humans:

| Tablet | mg/tablet |
|---|---|
| Compound NRC-2694 | 50 |
| Lactose anhydrous (USP) | 156 |
| Microcrystalline cellulose (Avicel pH102) | 15 |
| Sodium lauryl sulfate | 5 |
| Sodium starch glycolite | 10 |
| Povidone K-30 | 3 |
| Hydroxy propyl cellulose (LH-11) | 10 |
| Magnesium stearate | 1 |

We claim:

1. A method of treating lung cancer in a subject in need thereof, comprising:
administering to the subject an effective amount of a quinazoline derivative of formula (I) wherein:

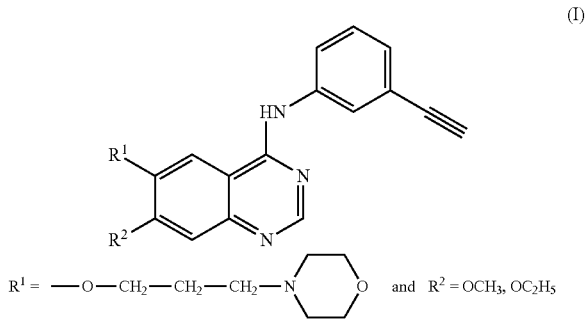

$R^1 = $ —O—$CH_2$—$CH_2$—$CH_2$—N⟨O⟩ and $R^2 = OCH_3, OC_2H_5$ or a pharmaceutically acceptable salt thereof.

2. The method of claim 1, wherein the quinazoline derivative of formula (I) has

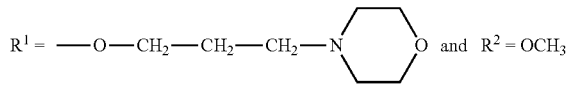

or a pharmaceutically acceptable salt thereof.

3. The method of claim 2, wherein the pharmaceutically acceptable salt is a monohydrochloride.

4. The method of claim 2, wherein the pharmaceutically acceptable salt is a dihydrochloride.

5. The method of claim 1, comprising administering a pharmaceutical composition comprising the quinazoline derivative of formula (I).

6. The method of claim 5, wherein the pharmaceutical composition comprises the quinazoline derivative of formula (I), lactose, microcrystalline cellulose, sodium lauryl sulfate, sodium starch glycolite, polyvinyl pyrrolidone, hydroxypropyl cellulose, and magnesium stearate.

* * * * *